United States Patent [19]

Wiltfong

[11] Patent Number: 5,001,630

[45] Date of Patent: Mar. 19, 1991

[54] COMPUTERIZED CASE HISTORY BUSINESS METHOD

[76] Inventor: M. J. Wiltfong, 3132 N. 108th St., Omaha, Nebr. 68164

[21] Appl. No.: 286,799

[22] Filed: Dec. 20, 1988

[51] Int. Cl.$^5$ ............................................. G06F 15/42
[52] U.S. Cl. ................................. 364/401; 364/413.01
[58] Field of Search ............... 364/401, 413.01, 413.02

[56] References Cited

U.S. PATENT DOCUMENTS

| | | | |
|---|---|---|---|
| 4,290,114 | 9/1981 | Sinay | 364/413.02 |
| 4,839,822 | 7/1989 | Dormond et al. | 364/413.02 |
| 4,858,121 | 8/1989 | Barbar et al. | 364/413.01 |

*Primary Examiner*—Michael R. Fleming
*Assistant Examiner*—Gail O. Hayes
*Attorney, Agent, or Firm*—James Creighton Wray

[57] ABSTRACT

This invention allows the user to tailor the system to his needs through the use of the following innovative methods. The catalog is a user defined selection screen of fifty numbered work-ups or procedures performed by the office or business. One, or a group of unique alphanumerical indicators are selected by the user to form a chain. Each chain is assigned a unique number by the user. Any chain may be assigned to any of the fifty abbreviated work-ups or procedures displayed on each catalog selection screen. A coded unique alphanumeric indicator has been assigned to each procedure, term, or remark in the provided, and user expansible, procedural index.

12 Claims, 2 Drawing Sheets

COMPUTERIZED CASE HISTORY BUSINESS METHOD

BACKGROUND OF THE INVENTION

Large and small offices have needs for modern-day computerized systems which reduce or eliminate much of the paper work of the past. Especially in modern offices with rapid turnover of staff, it is important to provide immediate access to all services rendered and to all verbal communications between the office personnel and the customer or client.

Each office or business, even in the same field, has unique needs for its record-keeping and marketing strategy. Existing systems of office automation often require strict adherence to procedures or methodology established for other offices or businesses. It is difficult or sometimes impossible to adapt to such a system because of these differences. Systems designed for a particular user are expensive and usually inflexible.

It probably is impossible to construct a system that will meet every desire, request, or demand of every office and business. However, it is the intention of this invention to construct a system that could be "user-defined" to adapt to the unique and varying needs of each office and business without changing the coding and program requirements established in the system. To accomplish this, it required certain unique and ingenious methods of flexibility to the presenting of material and the entering of responses.

SUMMARY OF THE INVENTION

The present preferred method of building office records includes entering customer, owner or client identifying information and displaying any communications, transactions, services, instructions, charges, or treatments records in response thereto. To obtain these displays for a specific office or business, this preferred method presents a "user" defined "catalog" screen listing the most common work-ups or procedures used in that office or business. The entering of a number selection from the "catalog" will identify the current work-up or procedure from the list that is to be entered. This will activate a "user" defined "chain" which automatically presents "user" defined procedures, terms, or remarks that the "user" has selected from the "procedural index" list. The "procedural index" which is made up of several thousands of procedures, terms and remarks that might be used in the office or business can be broadened to include any procedure, term or remark that is felt to be necessary in the function of that specific office or business. Each entry in the "procedural index" is given an "alphanumerical indicator". The "chains" are the groupings of "alphanumerical indicators" indicating pre-selected procedures, terms, or remarks that the "users" has chosen from the "procedural index". A "chain" may have one or several "alphanumerical indicators". Each "chain" by these assigned indicators identifies the screens to be sequentially presented. Each varied screen requires entry of varied manual answers or responses as the screens are presented. Appointments, reminders, inventory used, financial charges, historical transactions, and other such records are all maintained through this same method of manual responses to the presented screens activated by the "alphanumerical indicators" placed in the "chains" and triggered by an number entry at the "catalog".

The following word definitions are used with the invention:

| | | |
|---|---|---|
| "Alphanumerical Indicator" | = | a code system of a 5 digit number or a letter and a 5 digit number used to identify each entry, or "procedure, term, or remark" found in the "procedural index" listings. |
| | 1. | "procedures" require a letter with the 5 digit number. Each "procedure" is assigned to a "category". Each "procedure" requires a financial consideration. |
| | 2. | "terms and remarks" require only a 5 digit number. No "category" assignment or financial consideration is required. |
| "Procedural Index" | = | A list of several thousands of "procedures, terms, or remarks" |
| "procedure, terms, or remarks": | | Examples as used in the Medical field |
| procedure | = | Tonsillectomy, radiograph, blood count, etc. Financial consideration is required. |
| terms | = | Arm, leg, virus, seizure, cast cell, etc. No financial consideration is required. |
| remarks | = | Instructions, remarks, direction, report, etc. No financial consideration is required. |
| "category" | = | Are the 26 major groupings as defined by the "user". Example: In the medical field, these might be, examination, surgery, laboratory, etc. Each "procedure" listed in the "procedure index" is given a letter as part of the "alphanumerical indicator". Since all "procedures" require a financial considerations, the time used and money generated may be figured on a "category" level. |
| "Chain" | = | One or more "alphanumerical indicators" that are "user" selected and grouped with an identifying number up to 100. Any one of these groups can be assigned by the "user" to one of the fifty numbers that appear on the "catalog". |
| "Catalog" | = | A "user" defined selection screen that displays abbreviated "work-ups or procedures". |
| "work-up or procedures" | = | Common "work-ups or procedures" as defined by |

| | |
|---|---|
| | the "user" to appear on the "catalog". |
| "User" | = The office or party that has designed or defined the system to fit the needs thereof. |

The preferred method further includes the preliminary steps of grouping all "procedures" listed in the "procedural index" in 26 broad "categories" that are pertinent within the "users" specific office or business. Each procedure will have a letter in it's "alphanumerical indicator" assignment to indicate which "category" is to apply. All these procedures in the "procedural index" require a financial consideration. All other "terms" or "remarks" in the "procedural index" do not require any financial queued response.

The preferred method further includes ten or more screens that are activated by the "alphanumerical indicator" pre-selected, pre-ordered by the "user" to each pre-assigned "chain" which in turn is triggered from the "user" defined "catalog". Each screen is different in lay-out and questions. To complete the varying presented questions the person entering the manual responses is required to follow a certain routine and consistency. This forces the entry of needed often repetitive facts and information consistent with the specific office or business and the specific work-up or procedure being performed. This method accomplishes this without memorized steps or menu selection.

The preferred method of preparing systematized work-ups or procedures includes creating a "catalog" having fifty choices of work-ups or procedures. Each work-up or procedure is listed with an identifying number. This listing will include the 50 most common technical and administrative steps used in the specific office or business. Selecting one of the 50 items from the list in effect selects a predetermined chain of screens or a chain of chains of screens.

The preferred method of preparing systematized work-ups or procedures allows the "user" to assign, disengage or re-assign any "chain" to any of the fifty "catalog" choices. The "user" is allowed to build 100 "chains". The "user" builds each "chain" by selecting a lettered "alphanumerical indicator" from the "procedural index". This will correspond to a work-up or procedure shown on the "catalog". The "user" may also broaden the "chain" by entering in any desired order 1 to 36 other "alphanumerical indicators" found in the "procedural index".

The preferred method further includes the repeated entries of additional "chains" by selecting other work-up or procedures specified on the "catalog" screen. This may be repeated as needed after completing the manual responses to the queues from each earlier selection step.

The preferred method also includes the building of "chains" without the using the "catalog" numerical selections. The procedure, term, or remark can be entered directly from the "procedural index". This can be done by entering a "alphanumerical indicator" or the written description of the procedure, term, or remark desired to be entered. With the "alphanumerical indicator" associated with each entry the screen sequence and queued responses are automatically presented.

The preferred method also has 10 additional "chains" available from the "catalog". These are not "user" defined but are coded into the system. The sequence of screens to each selection is, however, determined by it's "alphanumerical indicator" assignment.

The preferred method of preparing systematized work-ups or procedures is done by utilizing the "alphanumerical indicators" which give a unique code to every entry in the "procedural index". The "user" is allowed to expand to "procedural index" and the "alphanumerical indicators" to fit the needs of each specific office and business. When an "alphanumerical indicator" is used, it may be used in one or several "chains". For example the "Appointment due" screen identified by one indicator, may be placed in several "chains" associated with different catalog entries.

This preferred method of selecting systematized work-ups or procedure from the invention are apparent in the disclosure which includes the above and ongoing specification and claims and drawings. The pre-assigning "alphanumerical indicators" for each procedure, term, or remark that is placed in a provided "procedural index". The pre-selection, pre-ordering and pre-assigning "chains" with these "alphanumerical indicators". The building and structuring of "calalogs' to fit each "user's" office or business requirements. The assigning a "chain" to activate each choice on the "catalogs" all allow this invention to accumulate required, desired, and repetitive information without step memorization, outlines and menus.

DETAILED DESCRIPTION OF THE DRAWINGS

Figure 1:
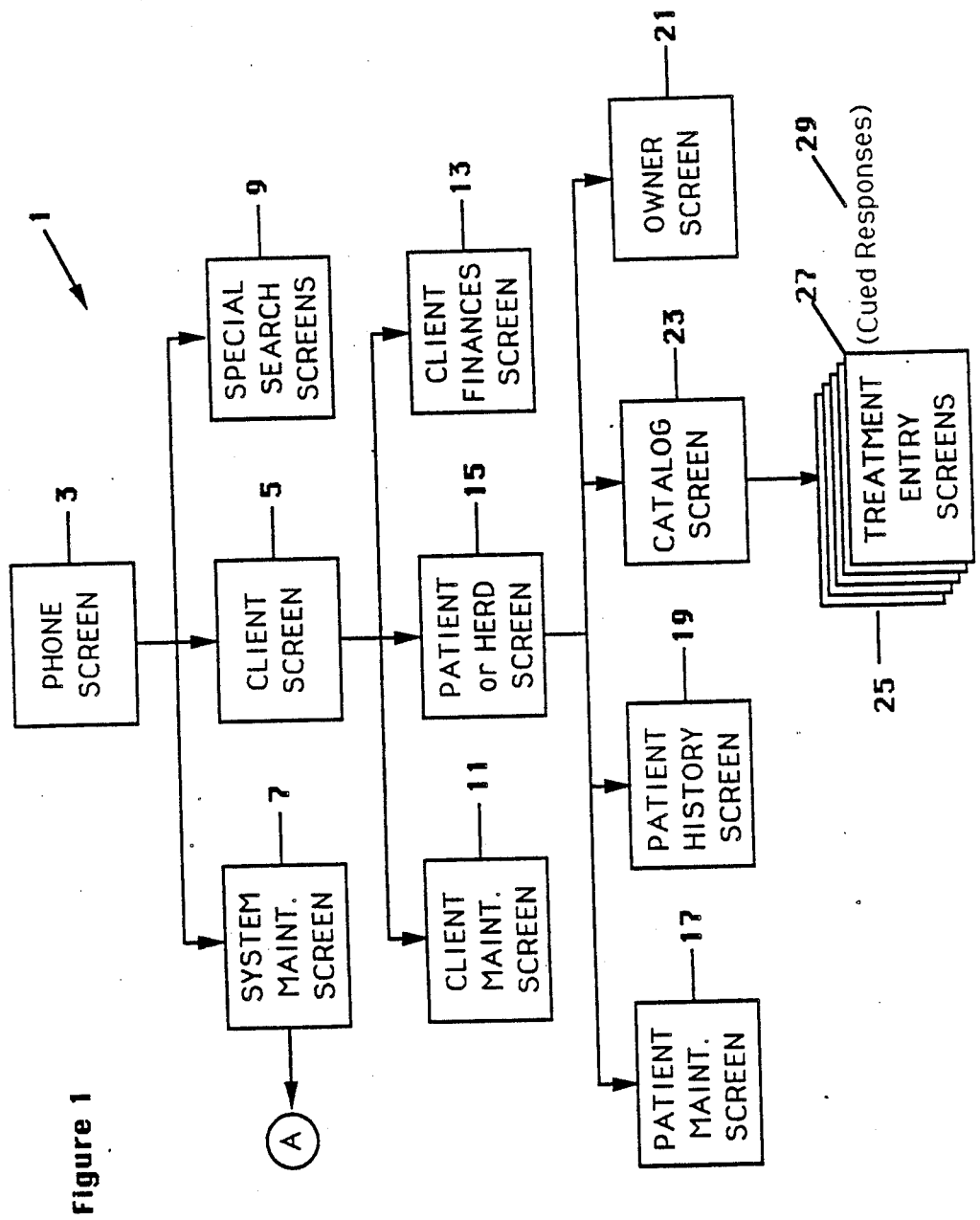
FIG. 1 is a flow chart positioning the use of the invention in a veterinary office application.
Figure 2:
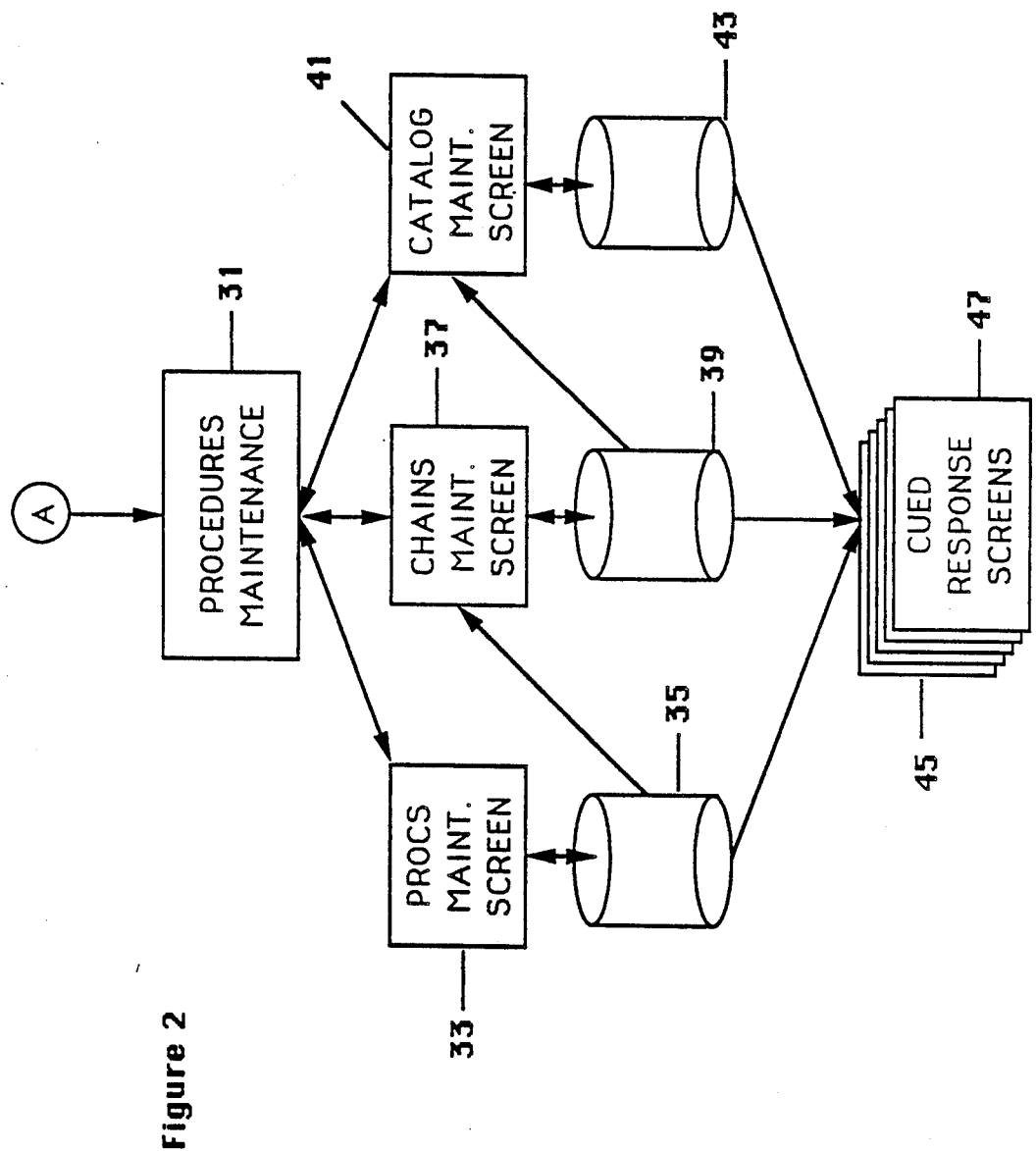
FIG. 2 is a flow chart indicating the processes used in forming the "procedural index", the "chains" and the "catalog."

Referring to FIG. 1, the outline 1 demonstrates the use of the invention in a veterinary application. FIG. 1 starts by a phone screen 3 where the client's phone number may be entered. If the client has never been entered, the person entering is allowed to record the client and any patients or species the person may have. When the phone is already present, the system displays the "client screen" 5. This screen will display all the previously entered patients or species entered for this client. An option at the "phone screen" 3 will display the "system maintenance screen" 7 with an option to move from FIG. 1 by "A" to the "*Procedures Maintenace" program which is the invention process as shown in FIG. 2. Special search screens 9 may be used to look for last names, patient names, breeds, or folder numbers to assist the "user" in finding the proper client. New individual patients or species entries are started at "client screen" 5. Changes to the "client screen" 5 may be entered directly. All financial transactions and reviews are also made from the "client screen" 5 by requesting the "client finances screen" 13. The person using the system may signify the desire to look at a certain individual or species that has already been entered. In the veterinary field an individual pet or a herd may be treated. This therefore requires separate screens for the individual patient and a herd screen depending on the situation involved. These two separate screens activate two totally different "calalogs" with each having their own unique "chains". When an individual or herd is entered, the system goes to either a "patient screen" 15 or "herd screen" 15 both with their own individual attributes and information. Changes may be made to the "patient screen" 15 or "herd screen" 15 by entering an option to display the "patient maintenance screen" 17. Treatment previously entered and posted may be reviewed from the "patient screen" 15 or "herd screen" 15 by entering the history option to display the "patient history screen" 19. "Owner screen" 21 may be displayed by selecting an owner information option on the "patient screen" 15 or "herd screen" 15. To enter new treatment, selecting the treatment option from the "patient screen" 15 or "herd screen" 15 will start the invention's manipulation of the sequence steps.

The option of treatment from the "patient screen" 15 or "herd screen" 15 will designate the desire to enter new treatment, work-up or procedures. One of two different "catalog screens" 23 appears depending if the access was from a "patient screen" or a "herd screen". Two "catalog" selection screens 23 are required since the work-ups or procedures would be entirely different for the "pet practice" and "farm practice".

Each "catalog screen" 23 will display its own list of 50 "user" defined work-ups or procedures used to enter the technical or administrative needs of the veterinary office or practice. The "catalog screens" would be similar to the pre-printed list of procedures in procedural billing slips or "peg board" entry as used in many non-automated offices. From the "catalog screens" 23, there is also an optional key to display an additional 10 special selections such as special instructions, reports, appointments, comments, etc. These 10 special selections are not "user" designed like the other fifty selections. They are, however, controlled by the "alphanumerical indicators" hard coded in the system to each of the ten selections.

To enter new treatment, work-up or procedures, the person using the system may select one or more of the fifty listed selections or the key option to display the other special selections. Each selection selected will trigger the pre-designed and pre-assigned "chain" 25 that will trigger specific screens 27 which require certain specific quequed responses 29 that need to be completed by the operator.

Manual responses are required to various queues 29 from the automatically presented screens 27. The varying responses are a result of the "alphanumberical indicator" assignment associated with a procedure, term or remark selected to meet the technical and administrative needs that are specific to the veterinary practice, the two pre-designed "catalog screens" 23 to list the more common work-ups or procedures used in the two types of veterinary practices, and the pre-designed "chains" 25 with each having been pre-assigned to one work-up or procedure appearing on one of the "catalog screens" 23.

The queued responses 29 are stored with pre-selected procedures, terms or remarks from the "procedural index". Therefore, all physical and verbal transactions with financial obligations can be stored and made accessible for the veterinary office.

Outline of the "Calalog" as used in Veterinary Medicine

Two "catalog screens" 23 are used in the veterinary medicine implementation. One is used for the individual patient or pet and the other is used for herd entry in the farm situation. Each "Catalog" 23 as used in the veterinary application is a list of 50 abbreviated work-ups or procedures, each identified by a unique number.

The invention allows the using office to designate, design and arrange the abbreviated descriptions of the most common work-ups or procedures to fit with any of the 50 numbers shown. By using this screen some consistent and routine methodology is achieved in each office or business.

The "system maintenance screen" 7 shown in FIG. 1 leads to the "procedures maintenance" 31 shown in FIG. 2. The "procedures maintenance screen" 33 may be displayed by an option from the "procedures maintenance" 31. The "procedures maintenance screen" 33 allows for the entering, storing and retrieval to and from an expandable memory 35 of 9,999-1 procedures for each of twenty six "categories". The procedures from memory 35 are grouped by the "chain maintenance screen" 37, which stores up to 100 chains in memory 39. "Catalog maintenance screen" 41 stores up to 50 catalog entries for the indiviaual pet and 50 entries for herd in storage 43. Each of the memories 35, 39, and 43 is used to display the variable screens activated by the "chains" 45 with the queued responses 47, which are related to the queued responses 29 of "treatment entry screens" 27 in FIG. 1.

The "catalog screen" 23 also has options to ignore any of the fifty listed work-ups and procedures and use any other procedure in the "procedural index" 35. Different procedures, terms, or remarks as listed in the index or their assigned "alphanumerical indicator" can be entered directly to build totally different work-ups or procedures. This direct approach still uses the "alphanumerical indicators" to sequence the "chains" 45 for queued responses 47. Also one of the "F keyed" options for entry at the bottom of the screen is for "OTHER/Selections". This option will trigger access to an additional 10 selections independent of the fifty numbered procedures. The "user" has no pre-selection or control over these additional 10 selections. These selections, however, still use the "alphanumerical indicators" assigned to each to give the screen sequence and queued responses.

Outlined of the "Chains" as used in Veterinary Medicine

Each numbered work-up or procedure on the "catalog screen" will need to be assigned at least one lead off "lettered" procedure from the "procedural index" 35. This initial procedure will require a manual financial declaration for the procedure that was selected. Other procedures, terms, or remarks from the "procedural index" 35 may or may not be assigned to follow the first procedure or any other entries as assigned. These selected procedures, terms, and remarks are identified entirely by their "alphanumerical indicator" assignment and placed in "user" ordered, designed and a assigned numbered "chain" 45. There may be as many as 100 constructed "chains" 45 stored by memory 39. These "chains" 45 may be "user" defined and assigned to or changed from any number designate shown on either of the "catalog screens" 23. Thereafter unless altered, the number entry designating the work-up or procedure entry from a "catalog screen" 23 will trigger the assigned "chain" 25 with it's designated "alphanumerical indicators". The "alphanumerical indicators" determine the screen sequence 27 and queued responses 29. The system is designed so that when using the "catalog screens" 23 and thereby the "chains" 25, each "chain" can be terminated early or expanded almost indefinitely to fit each situation. This is only possible because of the "alphanumerical indicators" and other index factors entered with each entry in the "procedural index" 35.

Outline of "Alphanumerical indicators" listed in the "Procedure Index" as used in Veterinary Medicine The present "procedure index" 35 for the verterinary application is a list of over 5,000 procedures", "terms", and "remarks" that might be needed to enter treatment, financial terms, and other pertinent information when performing the duties and services in the field. This index can be expanded to include 99,999 "procedures", "terms", and "remarks". Each of these entries is assigned an "alphanumerical indicator" which is the code of the invention that allows every step to be unique in screen sequence feeding.

"Procedure" is the term used to describe a work-up or a step used in treatment. All "procedures" used in this index will have a financial consideration to be entered. All "procedures" will have a letter with 5 numbers to the "alphanumerical indicator" assignment. The "procedures" with the letter assignments are grouped into 26 "user" defined "categories" which are common in a veterinary practice. Tonsillectomy, surgery, spay, castration, declaw, etc. would all be in a surgical "category". Bathing, nail trim, dipping, clipping etc. would all fall under a letter indicating a "category" of grooming. This letter assignment is also the external indicator to the system that a "Fee" screen is to be presented in the sequential steps of queue gathering responses.

"Term" is the work chosen to describe certain entries in the "procedural index" such as bone, leg, arm, virus, bacteria, etc. These are specific terms that might be needed to allow the office to enter certain comments, instructions, descriptions etc. in relationship to the item listed. These terms usually will only solicit statements and no financial charges so they are given only a five digit number and no letter in the "alphanumerical indicator" assignment. The system therefore ignores presenting any financial screen.

"Remark" is the word chosen to describe certain entries in the "procedural index" such as diagnosis, prognosis, remarks, reports, results, instructions, etc. These are specific remarks that might be needed to allow certain verbal instructions or thoughts to be expressed. Again since no financial obligations would be required, these remarks are assigned only a five digit number with no letter in the "alphanumerical indicator" assignment.

---

"PROCEDURAL INDEX" and "ALPHANUMERICAL INDICATOR" are described in the following Outline Each entry in the "Procedural Index" is assigned a five digit number.
Each entry in the "Procedural Index" that may require a financial
charge is assigned a letter followed by a five digit number.
    A. LETTERS - A LETTER in front of the number indicates:
        1. This "procedure" has been assigned to one of the 26 major
           "categories" found in the office or business.
        2. This selection from the "procedural index" will require a
           screen to enter a financial consideration.
    B. NUMBERS - All NUMBERS are coded or outlined to give unique
        screen sequences to each entry from the "catalog". This
        facilitates the obtaining of appropriate and required manual
        responses

| | |
|---|---|
| 1. Common Response screen | = any NUMBER over 01000. |
| 2. "COMMENTS" (long answers) screen | = 00120 |
| 3. "HMO's" package screen | = 00151 through 00185 |
| 4. I.D. number entry screen | = 00365, 00366, and 0367 |
| 5. Inventory dispensing screen | = 00400 through 00499 |
| 6. Inventory utilization screen | = 00500 through 00599 |
| 7. Follow up: Date and Reason | = 00600 through 00699 |
| 8. Follow up: Month and Reason | = 00700 through 00799 |
| 9. Quantity or # involved | = 00800 through 00999 |
| 10. "Fee" screen (indicated above) | = Any "LETTERED" entry |

Some of the Functions accomplished by the varying screens:
    A. Inventory used and quantity
    B. Printed instructions for inventory sold
    C. Appointment date and Reason
    D. Monthly reminders and Reason
    E. "Health Maintenance Options" and days for completion
    F. Quantity or number treated for groups
    G. Financial charges
    H. Sales tax charged
    I. Printed invoices
    J. Money revenue and time involved in each major department
    K. Money generated by each office personnel
    L. Time involved for each office personnel
    M. History of all transactions with manual entered responses
    N. Personal, confidential, and lengthy comments filed separately

---

While the invention has been described with reference to specific embodiments, modification and variations may be used with out departing from the scope of the invention which is described in the following claims.

I claim:

1. A business system comprising means for providing client histories, listing plural procedures, terms or remarks that may be used in a specific office or business, means for coding each listed procedure, term or remark with a distinct alphanumerical indicator, means for creating a procedural index of the alphanumerical indicators associated with the procedures, terms or remarks, means for providing a unique screen having prompters for operator responses for each procedure, term or remark associated with an alphanumerical indicator within the procedural index, means for listing common workups and overall procedures used in the office or business, means for relating sequentially several of the listed procedures, terms, or remarks to the listed common workups or overall procedures by identifying a particular list of alphanumerical indicators with each common workup or overall procedure entry, means for establishing chains of pre-selected and pre-ordered alphanumerical indicators, one chain being associated with each common workup or overall procedure, means for displaying the list of common workups or overall procedures on a catalog selection screen, means for selecting from the catalog screen one of the common workups or overall procedures, means for selecting a chain of pre-selected and pre-ordered alphanumerical ·indicators, and sequentially presenting screens related to each listed procedure, term or remark associated with that selected chain according to the selected pre-ordered chain, means for prompting operator responses with each screen presented means for and updating client histories with the selected workups or procedures and the operator responses, providing means for storing indications of selections of workups and overall procedures and operator responses, means for providing updating of case histories or services rendered, and responses entered, means for assigning each procedure listed within the procedural index to one of plural different categories, means for grouping in categories each of the listed procedures from the procedural index, means for assigning to each of the listed prod. procedures as indication of financial determination, the assigning comprising incorporating into each alphanumerical indicator related to a procedure a particular form of indicator.

2. The business system of claim 1 wherein the means for incorporating a particular form of indicator in the alphanumerical indicator associated with a procedure from the procedural index comprises incorporating a letter in the alphanumerical indicator.

3. The business system of claim 2 further comprising means for identifying each term or remark listed within the procedural index with a specific indicator which does not include a letter.

4. The business system of claim 3 further comprising means for identifying each term or remark listed within the procedural index with an indicator comprising five numbers.

5. The business system of claim 1 further comprising means for tailoring chains of alphanumerical indicators from the procedural index to be assigned to each workup or overall procedure listed on a catalog.

6. The business system of claim 5 further comprising means for tailoring and establishing plural chains of alphanumerical indicators to be assigned to specific workups and overall procedures listed on the catalog.

7. The business system of claim 1 further comprising means for creating a screen according to each entry in the procedural index and presenting the screens in sequence according to the chain of alphanumerical indicators associated with the selected catalog entry.

8. The business system of claim 7 further comprising means for building chains by entering procedures having particular signs and alphanumerical indicators in the procedural index.

9. The business system of claim 7 further comprising means for building chains by selecting procedures identified with alphanumerical indicators having letters in the procedural index.

10. The business system of claim 7 further comprising means for ending any chain by the operator prior to completion of the preselected and pre-ordered chain of alphanumerical indicators.

11. The business system of claim 7 further comprising means for expanding any chain by entering a procedure, term or remark or an alphanumerical indicator directly from the procedural index at the discretion of the operator.

12. The business system of claim 11 further comprising means for entering of one or more selections from the catalog and means for activating one or more preselected and pre-ordered chains to follow prior preselected chains.

* * * * *